United States Patent [19]

Everly et al.

[11] Patent Number: 4,483,800
[45] Date of Patent: Nov. 20, 1984

[54] PREPARATION OF 4-(α-ALKYL-α-CYANO-METHYL)-2,6-DI-SUBSTITUTED PHENOLS

[75] Inventors: Charles R. Everly; Gene C. Robinson, both of Baton Rouge, La.

[73] Assignee: Ethyl Corporation, Richmond, Va.

[21] Appl. No.: 510,886

[22] Filed: Jul. 5, 1983

Related U.S. Application Data

[63] Continuation-in-part of Ser. No. 385,609, Jun. 7, 1982, abandoned.

[51] Int. Cl.³ .................... C07C 121/75; C07C 69/66
[52] U.S. Cl. ........................ 260/465 F; 260/465 D; 260/465 E; 562/478
[58] Field of Search ........... 260/465 F, 465 D, 465 E; 562/478

[56] References Cited

U.S. PATENT DOCUMENTS

| | | | |
|---|---|---|---|
| 4,178,460 | 12/1979 | Berkelhammer et al. | 562/426 |
| 4,199,595 | 4/1980 | Berkelhammer et al. | 424/304 |
| 4,378,319 | 3/1983 | Stanley et al. | 260/465 F |
| 4,415,751 | 11/1983 | Greene | 562/478 |

OTHER PUBLICATIONS

Volod'kin et al., *Iz. Akad. Nauk. SSSR, Ser. Khim*, 1030–1032 (1966).
Kudinova et al., *Iz. Akad. Nauk. SSSR, Ser. Khim*, 1313–1317 (1978).
Schwartz et al., *J. Org. Chem.*, vol. 41, 2502 (1976).
Hay, *J. Org. Chem.*, vol. 34, 1160 (1969).
March, *Advanced Organic Chemistry*, (McGraw-Hill, New York, 1977), pp. 809–810.

*Primary Examiner*—Dolph H. Torrence
*Attorney, Agent, or Firm*—Donald L. Johnson; John F. Sieberth; Willard G. Montgomery

[57] ABSTRACT

4-(α-hydrocarbyl-α-cyano-methyl)2,6-di-substituted phenols having the formula

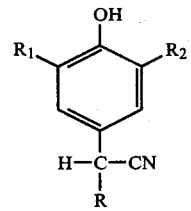

wherein R is selected from hydrogen, hydrocarbyl radicals, substituted hydrocarbyl radicals and hydrocarbyloxy radicals and $R_1$ and $R_2$ are the same or different monovalent substituent selected from the group consisting of alkyl, aralkyl and cyclic alkyl radicals and are prepared by reacting a di-substituted phenol having the formula

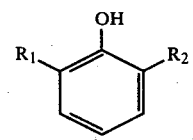

when $R_1$ and $R_2$ are as defined above with an aldehyde having at least one aldehyde radical and containing an R group as defined above and an alkali metal cyanide or an alkaline earth metal cyanide in a suitable solvent. The 4-(α-hydrocarbyl-α-cyano-methyl)2,6-di-substituted phenol thus formed can readily be converted to the corresponding 4-(α-hydrocarbyl-α-cyano-methyl)-phenol by dealkylating the substituent groups ortho to the hydroxyl group from the 4-(α-hydrocarbyl-α-cyano-methyl)-2,6-di-substituted phenol which then can be converted on hydrolysis to the corresponding α-hydrocarbyl-4-hydroxyphenylacetic acid. These acids are insecticidal and acaricidal intermediates and are deemed to have utility as insecticides themselves as are the 4-(α-hydrocarbyl-α-cyano-methyl)2,6-di-substituted phenols of the present invention.

23 Claims, No Drawings

PREPARATION OF 4-(α-ALKYL-α-CYANO-METHYL)-2,6-DI-SUBSTITUTED PHENOLS

CROSS-REFERENCE TO RELATED APPLICATION

This application is a continuation-in-part of pending Ser. No. 385,609, filed June 7, 1982, now abandoned.

TECHNICAL FIELD

This invention relates to certain novel 4-(α-hydrocarbyl-α-cyano-methyl)2,6-di-substituted phenols and to a novel process for their preparation. Further, this invention relates to 4-(α-hydrocarbyl-α-cyano-methyl)2,6-di-substituted phenols which are produced in a novel synthesis reaction and are used as intermediates in a reaction sequence in which α-alkyl-4-hydroxyphenylacetic acids are produced in which turn are used as reaction intermediates in the preparation of insecticides of m-phenoxybenzyl and α-cyano-m-phenoxybenzyl esters. The 4-(α-hydrocarbyl-α-cyano-methyl)2,6-di-substituted phenols of the present invention and the aforementioned acids also are deemed to have utility as insecticides in and of themselves.

BACKGROUND

Meta-phenoxybenzyl esters and α-cyano-m-phenoxybenzyl esters of 2-haloalkyl(oxy-, thio-, sulfinyl-, or sulfonyl)phenylalkanoic acids are known insecticidal and acaricidal agents. These compounds and methods for their preparation are disclosed in Berkelhammer et. al., U.S. Pat. Nos. 4,178,460 and 4,199,595. In both Berkelhammer et al. U.S. Pat. Nos. 4,178,460 and 4,199,595, there is disclosed the conversion of certain α-alkyl-3(or 4)-hydroxyphenylacetic acids having the formula

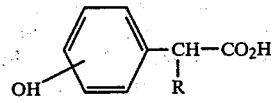

wherein R is ethyl, n-propyl or isopropyl to the corresponding α-alkyl-3(or 4)-difluoromethoxyphenylacetic acids having the formula

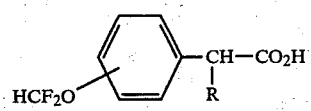

wherein R is as defined above by treatment with chlorodifluoromethane in aqueous alkali and dioxane. The α-alkyl-3(or 4)-difluoromethoxyphenylacetic acids thus formed can then be treated with thionyl chloride, thionyl bromide, or the like, preferably in the presence of an aromatic solvent such as benzene or toluene, to yield α-alkyl(substituted phenyl)acetyl halide which is reacted with m-phenoxybenzyl alcohol or α-cyano-m-phenoxybenzyl alcohol to yield the desired m-phenoxybenzyl ester or α-cyano-m-phenoxybenzyl ester of the 2-haloalkyl(oxy-, thio-, sulfinyl- or sulfonyl)phenylalkanoic acids which are useful insecticides. In Berkelhammer et. al., U.S. Pat. Nos. 4,178,460 and 4,199,595, αalkyl-3(or 4)-hydroxyphenylacetic acid intermediates are prepared by reacting the appropriate α-alkyl-3(or 4)-methoxyphenylacetonitrile with hydrobromic acid.

A new process for the synthesis of α-hydrocarbyl-4-hydroxyphenylacetic acids now has been discovered in which these materials can be prepared in a simple and straightforward manner. In this new process, 4-(α-hydrocarbyl-α-cyano-methyl)2,6-di-substituted phenols are produced in a novel synthesis reaction and are used as intermediates in a reaction sequence in which α-alkyl-4-hydrocyphenylacetic acids are likewise produced and used as reaction intermediates.

Methods are known for preparing 4-(αalkyl-α-cyano-methyl)2,6-di-substituted phenols. For example, the preparation of 4-(α-alkyl-α-cyano-methyl)2,6-di-substituted phenol by reacting α-alkyl-4-hydroxy-3,5-di-tertiary-butylbenzyl halides with sodium cyanide is reported by A. A. Vold'kin et. al., Iz. Akad. Nauk. SSSR, Ser. Khim, 1966, 1031. Also, the preparation of 4-(α-alkyl-α-cyano-methyl)-2,6-di-substituted phenol by the electrochemical reduction of the corresponding 2,6-di-substituted methylene-quinones is reported by L. I. Kudinova, et al., Iz. Akad. Nauk. SSSR, Ser. Khim., 1978, 1313. In U.S. application Ser. No. 385,610, entitled "Method of Preparing 4-(α-Alkyl-α-Cyano-Methyl)2,6-Di-Substituted Phenol", filed on June 7, 1982, now U.S. Pat. No. 4,405,528, there is disclosed a novel process for the synthesis of 4-(α-alkyl-α-cyano-methyl)2,6-di-substituted phenol by reacting a 2,6-di-substituted phenol with a Friedel-Crafts addition agent in the presence of a Friedel-Crafts catalyst such as aluminum chloride to form the corresponding 4-(α-alkyl-α-oxomethyl)2,6-di-substituted phenol, reducing the 4-(α-alkyl-α-oxomethyl)2,6-di-substituted phenol to form the corresponding 4-(α-alkyl-α-hydroxy-methyl)2,6-di-substituted phenol and thereafter reacting the 4-(α-alkyl-α-hydroxy-methyl)2,6-di-substituted phenol with an alkali metal or an alkaline earth metal cyanide to form the desired 4-(α-alkyl-α-cyano-methyl)2,6-di-substituted phenol.

The synthesis of o- and p-hydroxy substituted phenylacetonitriles also is known and is reported in the literature. See, for example, Journal of Organic Chemistry, Vol. 41, No. 14, 2502 (1976).

THE INVENTION

This invention thus involves in one embodiment the discovery that 4-(α-hydrocarbyl-α-cyano-methyl)2,6-di-substituted phenols can be readily prepared in good yield with high selectivity by reacting a 2,6-di-substituted phenol with an aldehyde and an alkali metal cyanide or an alkaline earth metal cyanide in a suitable reaction solvent to form the corresponding 4-(α-hydrocarbyl-α-cyano-methyl)2,6-di-substituted phenol.

The invention also involves in another embodiment that certain of these 4-(α-hydrocarbyl-α-cyano-methyl)2,6-di-substituted phenols are novel compounds.

In another embodiment of this invention, α-hydrocarbyl-4-hydroxyphenylacetic acid is produced by (1) forming a 4-(α-hydrocarbyl-α-cyano-methyl)2,6-di-substituted phenol in the above manner, (2) dealkylating the substituent groups ortho to the hydroxyl group from the 4-(α-hydrocarbyl-α-cyano-methyl)2,6-di-substituted phenol to produce a reaction product containing a substantial amount of the corresponding 4-(α-hydrocarbyl-α-cyano-methyl)phenol, and (3) thereafter converting the 4-(α-hydrocarbyl-α-cyano-methyl)-phenol to the corresponding α-hydrocarbyl-4-hydroxyphenylacetic acid by hydrolysis.

The phenols which may be used as starting materials in the process of the invention are phenols having the general formula

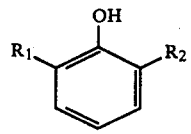

wherein each R is the same or different monovalent substituent selected from the group consisting of alkyl, aralkyl and cyclic alkyl radicals. These phenols are reacted in a liquid phase with an aldehyde and an alkali metal or an alkaline earth metal cyanide.

Typical examples of alkyl, aralkyl and cyclic alkyl radicals which $R_1$ and $R_2$ may be include any of the above radicals having any number of carbon atoms as long as these substituents do not interfere either with the formation of the desired 4-(α-hydrocarbyl-α-cyano-methyl)2,6-di-substituted phenol or with the subsequent dealkylation of the 4-(α-hydrocarbyl-α-cyano-methyl)2,6-di-substituted phenol to produce the corresponding 4-(α-hydrocarbyl-α-cyano-methyl)phenol. These may include, for example, from 1 to 40 or more carbon atoms and the alkyl radicals may include primary, secondary or tertiary alkyl groups and cycloaklyl groups. Since the most readily available of the substituted phenols are those phenols having substituents of from 1 to about 8 carbon atoms they are preferred, but the invention is not limited thereto. Examples of typical substituents include methyl, ethyl, propyl, isopropyl, the isomeric butyl radicals (i.e., n-butyl, isobutyl, cyclobutyl, t-butyl, etc.), the isomeric amyl radicals, the isomeric hexyl radicals, the isomeric decyl radicals, the isomeric hexadecyl radicals, the isomeric eicosyl radicals, the isomeric tricosyl radicals, the isomeric triacontyl radicals, etc. The alkyl radicals may be substituted with aryl, preferably monocyclic aryl radicals, or cycloalkyl radicals, for example, benzyl, phenylethyl, cyclohexylethyl, naphthylethyl, etc. Examples of aryl radicals are phenyl, tolyl, xylyl, biphenylyl, naphthyl, methylnaphthyl, ethylphenyl, cyclohexylphenyl, etc. Because the phenols in which the R substituents are methyl, ethyl, propyl, butyl, sec-butyl, isopropyl, t-butyl, amyl, sec-amyl, t-amyl, hexyl, heptyl, octyl, etc., or phenyl are either readily available commercially or easily made and are ideally suited for the process, the most preferred substituents are where $R_1$ and $R_2$ are a lower alkyl group (i.e., from 1 to about 8 carbon atoms) or phenyl.

Examples of phenols having the R substituent groups noted above which are preferred starting materials include 2,6-di-methylphenol, 2,6-di-sec-butylphenol, 2,6-diisopropylphenol, 2,6-di-sec-octyl-phenol, 2,6-di-(α-methylbenzyl)phenol, 2-amyl-6-methyl-phenol, 2,6-dibenzylphenol, 2-methyl-6-benzylphenol and the like. A particularly preferred phenol reactant for use in the practice of the process is 2,6-di-tert-butylphenol.

Substituent R groups other than those previously listed such as aryl, chlorine, bromine, fluorine, nitro groups, and the like may be present at the 2- and 6- positions in the aromatic phenol compound providing they do not adversely affect the formation of the 4-(α-hydrocarbyl-α-cyano-methyl)2,6-di-substituted phenol or the subsequent dealkylation of the condensation reaction product to the corresponding 4-(α-hydrocarbyl-α-cyano-methyl) henol.

The aldehyde reactant used in the process is an aldehyde having at least one aldehyde radical and contains an R group selected from hydrogen, hydrocarbyl radicals, substituted hydrocarbyl radicals and hydrocarbyloxy radicals. Preferably, the hydrocarbyl radicals are those that contain up to about 30 carbon atoms. The more preferred hydrocarbyl radicals are those that contain up to about 20 carbon atoms. For purposes of this invention a hydrocarbyl radical can be defined as hydrogen or an organic group solely composed of hydrogen and carbon atoms. Some non-limiting representative examples of hydrocarbyl radicals are alkyl, cycloalkyl, alkenyl, aralkyl, alkaryl, and aryl.

Examples of suitable alkyl groups are methyl, ethyl, n-propyl, isopropyl, n-butyl, isobutyl, sec-butyl, tert-butyl, n-amyl, and the various positional isomers thereof, and likewise the corresponding straight and branched chain isomers of hexyl, heptyl, octyl, nonyl, decyl, undecyl, dodecyl, and the like.

Some examples of cycloalkyl groups are cyclopropyl, cyclobutyl, cyclopentyl, cyclohexyl, cycloheptyl, cyclooctyl, cyclononyl, cyclodecyl, cycloundecyl, cyclododecyl, and the like. They may also be such cycloaliphatic groups as α-cyclopropylethyl, α-cyclobutyl-propyl, β-cyclobutyl-propyl, and similar alkyl derivatives of the higher cycloalkyls.

some examples of alkenyl groups are ethenyl, 1-propenyl, 2-propenyl, isopropenyl, 1-butenyl, 2-butenyl, 3-butenyl, and the corresponding branched-chain isomers thereof as for example, 1-isobutenyl, 2-isobutenyl, 2-sec-butenyl, including 1-methylene-2-propenyl, and the various isomers of pentenyl, hexenyl, heptenyl, octenyl, nonenyl, decenyl, undecenyl, and dodecenyl, including 3,3-dimethyl-1-butenyl, 2,3-dimethyl-1-butenyl, 2,3-dimethyl-2-butenyl, 2,3-dimethyl-3-butenyl, 1-methyl-1-ethyl-2-propenyl, and the like.

Examples of alkaryl groups are tolyl, 2,3-xylyl, 2,4-xylyl, 2,5-xylyl, 2,6-xylyl, 3,4-xylyl, 3,5-xylyl; o, m, and p-cumenyl, mesityl, o, m, and p-ethylphenyl, 2-methyl-1-naphthyl, 3-methyl-naphthyl, 4-methyl-1-naphthyl, 5-methyl-2-naphthyl, 6-methyl-3-naphthyl, 7-methyl-1-naphthyl, 8-methyl-4-naphthyl, 1-ethyl-2-naphthyl, and its various positional isomers and the like.

Examples of aryl groups which may be present in the above general formula are phenyl, naphthyl, and the like.

Examples of aralkyl groups are benzyl, phenylethyl, 1-phenylpropyl, 2-phenylpropyl, 3-phenylpropyl, 1- and 2-isomers of phenylisopropyl, 1-, 2-, and 3-isomers of phenylbutyl, and the like.

The substituted hydrocarbyl radicals are hydrocarbyl radicals which contain substituents such as halogen, hydroxyl, carboxyl, amino, or amide radicals.

As mentioned above, the hydrocarbyl groups may be halogen substituted. Thus, chlorine, bromine, iodine, and fluorine may be substituted on the alkyl, cycloalkyl, alkenyl, alkaryl, aryl, and aralkyl groups which are present. Non-limiting examples of such substituted groups are chloromethyl, chloroethyl, bromethyl, 2-fluoro-1,2-dibromoethyl, 1-iodopropyl, 2-fluoropropyl, 1-chlorobutyl, 2-bromobutyl, 2-iodo-2-methylpropyl, 1-chloropentyl, 3-fluoro-2methylbutyl, 3-iodo-2-methylbutyl, 1-chloro-2,2-dimethylpropyl, 2-chloroheptyl, 3-fluorononyl, 1-chlorododecyl, and the like. Examples of halogenated cyclo-alkyl groups are chlorocyclopropyl, chlorocyclohexyl, 1,2- dichlorohexyl, bromocyclobutyl, iodocyclohexyl, and the like.

Examples of halogen-substituted alkenyl groups are bromoethenyl, chloroethenyl, iodoethenyl, 1-bromododecenyl, and the like.

Examples of halogenated alkaryl groups are chloro-o-tolyl, chloro-p-tolyl, chloro-m-tolyl, 2-bromo-3,4-xylyl, 4-bromo-2,3-xylyl, 5-bromo-2,4-xylyl, 2-bromo-4,5-xylyl, 3-bromoesityl, chloro(methyl)-1-naphthyl, iodo(ethyl)-1-naphthyl, all positional isomers of the above, and the like.

Examples of halogen substituted aryl groups are bromophenyl, 2-bromo-1-naphthyl, 3-bromo-1-naphthyl and all positional isomers thereof, 2,4-dibromophenyl, 2,3-dibromophenyl, 2,5-dibromophenyl, 2,3,4,5-tetrabromophenyl, 2,3,5,6-tetrabromophenyl, pentabromophenyl, all isomers of chlorophenyl, and all isomers of multichlorophenyl: 2-choro-1-naphthyl and the remaining isomers thereof: 2,3-dichloro-1-naphthyl, 2,4-dichloro-1-naphthyl and the remaining positional isomers of dichloronaphthyl, 2,3,4,5-tetrachloro-1-naphthyl.

Amine groups may also be substituted on the hydrocarbyl groups. Some non-limiting illustrative examples of hydrocarbyl groups containing amine substituents are aminomethyl, 2-aminoethyl, 2,2-diaminoethyl, 2-aminoisopropyl, 5-aminopentyl, 1,2-aminododecyl, 1,2-diaminoethyl, 1,5-diaminopentyl, aminocyclobutyl, aminocyclohexyl, 3-amino-1-propen-1-yl, 5-amino-2-penten-1-yl, aminophenyl, (methylamino)phenyl, 2-amino-o-tolyl, 4-amino-m-tolyl, 3-amino-p-tolyl, and other positional isomers, various isomers of diaminophenyl, amino-2,5-xylyl, and various positional isomers thereof, 2-amino-1-naphthyl, 3-amino-1-naphthyl, 2-amino-3-methyl-1-naphthyl, 2,3-diamino-5-ethyl-1-naphthyl, and the like.

The hydrocarbyl groups may contain amide groups which may be illustrated by such non-limiting examples as: carbamoylmethyl, 2-carbamoylethyl, 4-carbamoylbutyl, 8-carbamoyl-2-ethyloctyl, 1,4-dicarbamoylbutyl, carbamoylcyclopentyl, carbamoylcyclohexyl, 2-carbamoyl-o-tolyl, 2-carbamoyl-m-tolyl, 3-carbamoyl-p-tolyl, (carbamoylmethyl)phenyl, (2-carbamoylethyl)benzyl: o-, m-, and p-(carbamoylethyl)phenyl, and the like.

The alkali earth and alkaline earth metal cyanide reactants used in the present process may include sodium cyanide, potassium cyanide, lithium cyanide, magnesium cyanide and calcium cyanide. Ammonium cyanide also may be used in the practice of the process as well as hydrogen cyanide. Sodium cyanide is a preferred cyanide reactant.

The reaction is carried out in the liquid phase which is provided by using a solvent which is inert under the reaction conditions. That is, the reaction is carried out in the presence of a solvent which does not enter into the reaction. Preferred solvents are aprotic solvents which include ethers such as diethyl ether, dibutyl ether, 1-ethoxyhexane, tetrahydrofuran, 1,4-dioxane, 1,3-dioxolane, diglyme, 1,2-diethoxyethane and tertiary amines such as pyridine, N-ethylpiperidine, triethylamine, tributylamine, N,N-diphenyl-N-methyl amine, N,N-dimethylalanine, etc. Especially preferred solvents are dipolar aprotic solvents such as dimethyl sulfoxide, N,N-dimethylformamide, N,N-dimethylacetamide, dimethyl sulfone, tetramethylene sulfone, N-methylpyrrolidinone, acetonitrile and like materials. Other solvents which are inert under the reaction conditions may be used: for example, low boiling hydrocarbons, halogenated hydrocarbons, examples of which are benzene, toluene, tetrachloroethane, the chlorinated benzenes, the chlorinated toluenes, etc. Additionally, lower alkanols having up to about 6 carbon atoms also may be used. These include methanol, ethanol, n-propanol, isopropyl alcohol, n-butanol, sec-butyl alcohol, tertbutyl alcohol, n-pentanol, isopentyl alcohol, n-hexanol and isohexyl alcohol. In addition, a small amount of water may be added to the reaction mixture to facilitate the solubilization of the cyanide-containing reactant in the mixture.

The reaction is readily conducted by placing the 2,6-di-substituted phenol and the other reaction mixture components in a reaction vessel having agitation means. The process is preferably conducted in a substantially anhydrous reaction system, and accordingly, the components of the reaction system should be brought together and maintained under a substantially dry, inert atmosphere. Thus, while it is possible to conduct this process in the presence of air or moisture, as when water is added to the reaction mixture, it is desirable to maintain the reaction system under an atmosphere of dry nitrogen or the like.

The mode of addition is not particularly critical. Accordingly, it is convenient to add the phenol reactant to a mixture of the other materials, add the aldehyde reactant to a mixture of the other materials, add the cyanide reactant to a mixture of the other materials, introduce all ingredients simultaneously into the reaction zone or the like. The process should be carried out for a time sufficient to convert substantially all of the phenol reactant to the corresponding 4-(α-hydrocarbyl-α-cyanomethyl)2,6-di-substituted phenol intermediate. In general, the length of time for optimum yield depends primarily on the reaction temperature and the particular solvent used in the reaction. However, reaction ordinarily proceeds very rapidly, and thus, long reaction times are not required. The reaction can be completed in the matter of minutes or at most a few hours at the reaction conditions.

Although the reaction will proceed at a very slow rate at ambient temperatures, it is convenient to conduct the reaction at an elevated temperature of at least about 50° C. up to the decomposition temperature of any of the reactants or the products. Ambient atmospheric pressure can be used or pressures lower or higher than ambient pressure can be used. However, there is no advantage to using less than ambient pressure. Higher than ambient pressure conditions are usually used if temperatures higher than the boiling point at atmospheric conditions of the reaction mixture are being used. However, by proper choice of the solvent to form the liquid phase desired, temperatures can be reached within the range of about 50° C. up to the reflux temperature of the reaction mixture at ambient atmospheric conditions which gave a suitable reaction rate.

Conversion of the 2,6-di-substituted phenol reactant to the corresponding 4-(α-hydrocarbyl-α-cyanomethyl)2,6-di-substituted phenol in accordance with the practice of the invention results in substantially very little by-product formation, such as unreacted phenol, and 4-(α-hydrocarbyl-α-methyl)2,6-di-substituted phenol. Recovery of the product is achieved by conventional means such as evaporation and water or extraction with a suitable organic solvent.

For best results, it is desirable to employ an excess of both the aldehyde and cyanide reactants relative to the 2,6-di-substituted phenol reactant. Normally, the reaction system will contain at least one molar equivalent of aldehyde and one molar equivalent of cyanide per mole of phenol reactant and preferably the molar ratio of the aldehyde and te cyanide to the phenol is 2 or more.

In general, any of the various dealkylation procedures using conditions and catalysts known in the art for causing dealkylation may be used in removing the substituent groups ortho to the hydroxyl group from the 4-(hydrocarbyl-α-cyano-methyl)2,6-di-substituted phenol to produce a reaction product containing a substantial amount of the corresponding 4-(α-hydrocarbyl-α-cyano-methyl)phenol intermediate providing they do not interfer with the course of the reaction. Preferably, dealkylation is achieved in high yield at elevated temperatures using an aluminum phenoxide or a Lewis acid catalyst in the presence of an aromatic or substituted aromatic compound. The conditions used for such dealkylations are well known and are reported in the literature. See, for example, *Journal of Organic Chemistry* Vol. 34, 1160 (1969) and references cited therein, all disclosures of which are incorporated herein by reference.

The dealkylation process most conveniently employed comprises heating the 2,6-di-substituted phenol at an elevated temperature below the decomposition temperature of the desired 4-(α-hydrocarbyl-α-cyano-methyl)phenol intermediate product, such as from about 60° C. to 250° C. in the presence of a dealkylation catalyst and an aromatic hydrocarbon or a substituted aromatic hydrocarbon, such as, for example, benzene, toluene, xylene and the like. Although it is not a requirement of the dealkylation process, the reaction can be carried out under an inert, nonreactive atmosphere, such as nitrogen, if desired.

In the reaction, the aromatic compound serves both as a solvent for the reaction and as an acceptor for the substituent groups ortho to the hydroxyl group in the 4-(α-hydrocarbyl-α-cyano-methyl)2,6-di-sbstituted phenol reactants which are dealkylated in a transalkylation process. Dealkylation results in the formation of substituted aromatic by-products, such as, for example, a mixture of ortho and para-tertiary-butyl toluene when toluene is employed as the aromatic compound in the reaction from which the desired 4-(α-hydrocarbyl-α-cyano-methyl)phenol intermediate product can be separated and recovered using well-known techniques such as distillation, fractional distillation, crystallization or extraction techniques, etc. It is not necessary, however, to first recover the desired intermediate phenol product from the reaction mixture prior to subsequent hydrolysis of the intermediate to the corresponding acid. For best results, it is desirable to employ an excess of aromatic or substituted aromatic compound relative to the di-substituted phenol reactant. Normally, the reaction system will contain at least 2 molar equivalents of aromatic reactant per mole of alkylated phenol reactant and preferably the molar ratio of the aromatic reactant to the alkylated phenol reactant is more than 2.

Aromatic hydrocarbons or substituted aromatic hydrocarbons which may be used in the dealkylation reactant include benzene, toluene, ethylbenzene, xylene, trimethylbenzene, tetrahydronaphthalene, isobutylbenzene, phenols (e.g., phenol, cresol, O-isopropylphenol, 4-hydroxyanisole, mono-, di-, and tribromophenol, etc., halobenzenes (e.g., mono-, di-, and trifluorobenzenes, chlorobenzenes, bromobenzens, chlorobromobenzenes), aromatic ethers (e.g., anisole, diphenylether, etc.), and the like.

Dealkylation of the substituted phenol in accordance with the invention is conducted, for example, by charging to a suitable reaction vessel the substituted phenol of choice, the solvent and the dealkylation catalyst, optionally under a blanket of nitrogen, and then heating to a temperature below the decomposition temperature of the desired 4-(α-hydrocarbyl-α-cyano-methyl)-phenol intermediate product, but high enough to effect dealkylation of the substituted phenol.

As pointed out hereinabove, the dealkylation reaction can be conducted over a wide temperature range below the decomposition temperature of the desired dealkylated product. While the reaction will proceed at ambient temperatures at a very slow rate, in general, dealkylation is carried out at a temperature range of from about 60° C. to about 250° C. and will vary within this range depending upon the solvent of choice.

In general, dealkylation is carried out at atmospheric pressure although pressures above atmospheric pressure can be used if desired.

The dealkylation reaction should be carried out for a time sufficient to convert substantially all of the substituted phenol starting material to the desired dealkylated phenol intermediate product. The length of time required to obtain substantially complete dealkylation of the substituted phenol will depend primarily upon the operating temperature and the particular substituted phenol used in the reaction.

A wide variety of catalysts known in the art for causing dealkylation may be used in the practice of the process. For example, dealkylation catalysts such as phenoxy derivatives of such elements as aluminum, magnesium, iron, zinc, phosphorus, zirconium, titanium, bismuth, tin, etc., where the phenoxy moiety may be the phenoxy radical itself, the cresoxy radical, the xyloxy radical, etc. Also, Lewis acids, preferably aluminum chloride, zinc chloride, etc., which are predominantly para-directing catalysts when used as alkylation catalysts may be used for the dealkylation reaction. A most preferred dealkylation catalyst is aluminum chloride.

The amount of catalyst used is an amount sufficient to promote dealkylation of the substituted phenol reactant. While an amount as little as 0.1 mole percent up to amounts of about 20 mole percent based on the weight of the di-substituted phenol reactant can be used, for best results it is desirable to employ an even greater amountof catalyst up to, for example, 120 mole percent.

A variety of well-known hydrolysis procedures can be used for converting the 4-(α-hydrocarbyl-α-cyano-methyl)phenol to the corresponding α-hydrocarbyl-4-hydroxyphenylacetic acid. The hydrolysis can be performed in the presence of water and a suitable polar organic solvent such as low-molecular weight alcohols (e.g., methanol or ethanol), 1,4-dioxane, acetone, low-molecular weight carboxylic acids (e.g., acetic acid or propionic acid), N-methylpyrrolidinone, dimethylsulfoxide or the like.

While hydrolysis may be performed in a neutral system or an acidic system, basic hydrolysis is preferred. The reagent of choice is aqueous sodium hydroxide. Reaction temperatures will usually fall between 20° C. and the boiling point of the reaction medium. However, temperatures above the boiling point of the reaction medium can be utilized at elevated pressures to increase the rate of hydrolysis, if desired. These and other details of the hydrolysis reaction can be found in the literature—see, for example, March, *Advanced Organic Chemistry*, (McGraw-Hill, New York, 1977), pp. 809-10 and references cited therein, all disclosures of which are incorporated herein by reference.

The practice of this invention will be still further apparent by the following illustrative examples.

EXAMPLE 1

Preparation of (α-Cyano-Methyl)2,6-Di-Tertiary-Butyl Phenol 2,6-di-tertiary-butyl phenol (2.06 g.; 10 mmoles), sodium cyanide (1.47 g; 30 mmoles), paraformaldehyde (0.72 g.; 24 mmoles) and dimethylformamide (8 ml.) were charged to a 180 ml. Fischer-Porter tube and pressurized to 125 psig with nitrogen and heated to 140° C. (oil bath temperature) for 9 hourss. The resultant reaction mixture was allowed to cool to ambient temperature and the mixture was added to water, extracted with diethyl ether, the ether layer was dried (MgSO$_4$), filtered and the ether removed in a rotary evaporator to give a 56.4% yield of 4-(α-cyano-methyl)2,6-di-tertiary-butyl phenol as characterized by VPC.

EXAMPLE 2

Preparation of 4-(α-Isopropyl-α-Cyano-Methyl)2,6-Di-Tertiary-Butyl Phenol 2,6-di-tertiary-butyl phenol (21.42 g.; 103.8 mmoles), sodium cyanide (15.29 g.; 312 mmoles), isobutyraldehyde (17.99 g.; 250 mmoles) and dimethyl formamide (83 ml.) were charged to a 180 ml. Fischer-Porter tube and pressurized to 125 psig with nitrogen and heated to 140° C. (oil bath temperature) for 9 hours. The resultant reaction mixture was allowed to cool to ambient temperature and the mixture was poured into ~150 ml. of water, and extracted with diethyl ether. The ether layer was dried (MgSO$_4$), filtered and the ether removed in a rotary evaporator. The residue was dissolved in ~30 ml. of ethanol and precipitated by the slow addition of ice to yield 27.05 g. (90.7%) of 4-(α-isopropyl-α-cyano-methyl)2,6-di-tertiary-butyl phenol.

In a manner similar to Example 2 above, a number of experiments were carried out varying the temperature, reaction time, pressure, and ratio of reactants. The results were analyzed by vapor phase chromotography with internal standards and are shown in Table 1.

TABLE I

Preparation of 4-(α-Isopropyl-α-Cyano-Methyl)2,6-Di-Tertiary-Butyl Phenol

| Experiment No. | 2,6-di-tert-butyl phenol (mmoles) | Isobutyr-aldehyde (mmoles) | NaCN (mmoles) | Solvent (ml.) | Temp. (°C.) | Pressure (psig) | Time (hr.) | % Yield |
|---|---|---|---|---|---|---|---|---|
| 3 | 10 | 24 | 30 | DMF-8 ml. | 95 | 125 | 7 | 58.5 |
| 4 | 10 | 24 | 30 | EtOH-8 ml. | 140 | 125 | 7 | 47.0 |
| 5 | 10 | 24 | 30 | DMF-8 ml. | 135 | 125 | 7 | 78 |
| 6 | 80 | 192 | 240 | DMF-64 ml. | 140 | 125 | 9 | 86 |
| 7 | 10 | 24 | 30 | toluene-8 ml. | 135 | 125 | 5 | trace |
| 8 | 103.8 | 207.6 | 207.6 | DMF-83 ml. | 140 | 125 | 9 | 94.5 |
| 9 | 103.8 | 250 | 114.1 | DMF-83 ml. | 140 | 125 | 9 | 54.0 |
| 10 | 103.8 | 200 | 119.4 | DMF-83 ml. | 140 | 125 | 9 | 84.0 |
| 11 | 10 | 24 | 30 | isopropyl alc.-8 ml. | 95 | 125 | 7 | 14.2 |
| 12 | 10 | 12 | 30 | EtOH-8 ml. | 95 | 125 | 2.5 | 66.4 |
| 13 | 103 | 250 | 207 | DMF-83 ml. | 140 | 100 | 9 | 92 |
| 14 | 103 | 250 | 207 | DMF-83 ml./5% H$_2$O | 140 | 100 | 4 | 75 |
| 15 | 100 | 200 | 125 | DMF-83 ml./5% H$_2$O | 140 | 100 | 9 | 71 |
| 16 | 103.8 | 250 | 207 | DMF-83 ml./5% H$_2$O | 140 | 80 | 9 | 83.1 |
| 17 | 103.8 | 250 | 207.6 | MeOH-83 ml. | 140 | 105 | 5.5 | 91.7 |
| 18 | 103.8 | 175 | 155.7 | MeOH-83 ml. | 140 | 100 | 3 | 87 |
| 19 | 100 | 175 | 150 | MeOH-85 ml. | 140 | 80 | 3 | 95 |
| 20 | 100 | 150 | 125 | MeOH-85 ml. | 140 | 80 | 3 | 82.4 |

EXAMPLE 21

Preparation of 4-(α-Isopropyl-α-Cyano-Methyl)Phenol

A solution of 4-(α-isopropyl-α-cyano-methyl)2,6-di-tertiary-butyl phenol (30.37 g.; 106.2 mmoles) and 150 ml. toluene as charged to a reactor equipped with a stirrer, thermometer and reflux condenser. Aluminum chloride (17 g.; 127.5 mmoles) was added to the reactor vessel in 3 or 4 increments while vigorous agitation was maintained. An exotherm was observed which raised the reaction temperature by ~20° C. After the aluminum chloride addition was complete, the solution was heated to 95° C. for 5 hours under nitrogen. The reaction mixture was then cooled to ambient temperature, washed twice with water to remove aluminum salts formed during the reaction and the solvent and tertiary-butyl-toluene by-product was removed under reduced pressure to yield 20.1 g. (95.3%) of product determined by VPC (internal standard) as 4-(α-isopropyl-α-cyano-methyl)phenol.

In a manner similar to Example 21 above, a number of experiments were carried out varying the temperature, reaction time, ratio or reactants and catalysts. The results were analyzed by vapor phase chromotography with internal standards (unless otherwise indicated) and are shown in Table II.

TABLE II

Preparation of 4-(α-Isopropyl-α-Cyano-Methyl)Phenol

| Experiment No. | 4-(α-isoprpopyl-α-cyano-2,6-di-tertiary-butyl)phenol (g.) | Catalyst (g.) | Solvent (ml.) | Temp. (°C.) | Time (hr.) | % Yield |
|---|---|---|---|---|---|---|
| 22 | 4.80 | DEAC*-0.22 | — | 160 | 3 | |
| | | | | 175 | 2 | 36.3 - External Standard |
| 23 | 4.80 | DEAC-0.22 | — | 180–185 | 6 | 56.4 - External Standard |
| 24 | 5.92 | DEAC-0.24 | — | 195–200 | 6 | 82.5 - External Standard |
| 25 | 6.5 | AlCl₃-0.48 | — | 175–180 | 4 | 64.8 - External Standard |
| 26 | 6.5 | AlCl₃-0.47 | — | 195–200 | 5 | 67.6 - External Standard |
| 27 | 7.0 | DEAC-0.20 | — | 195–200 | 5 | 50.4 - External Standard |
| 28 | 6.8 | DEAC-0.48 | — | 200 | 5 | 55.0 - External Standard |
| 29 | 4.0 | TEA**-0.29 in toluene | — | 180 | 5 | trace |
| 30 | 4.26 | DEAC-0.29 | — | 180 | 5 | 63.2 |
| 31 | 3.75 | AlCl₃-0.30 | — | 180 | 5 | 68.0 |
| 32 | 5.04 | DEAC-0.30 in phenol | — | 195–200 | 5 | mostly starting material |
| 33 | 7.65 | AlCl₃-1.50 | — | 170 | 5 | 55.9 |
| 34 | 6.01 | AlCl₃-0.69 | — | 170 | 5 | 63.8 |
| 35 | 6.01 | AlCl₃-0.69 | toluene-4.5 | 140 | 5 | 14.7 |
| 36 | 4.54 | DEAC-0.20 | — | 170 | 5 | 38.4 |
| 37 | 7.67 | AlCl₃-0.60 | — | 170–175 | 5 | 45.4 |
| 38 | 6.86 | AlCl₃-4.00 | toluene-50 | 80–85 | 5 | 91.2 |
| 39 | 6.86 | AlCl₃-4.00 | toluene-50 | 100–105 | 5 | 94.2 |
| 40 | 8.11 | AlCl₃-4.45 | toluene-60 | 90 | 5 | 92.3*** |
| 41 | 24 | AlCl₃-11.40 | toluene-100 | 95–100 | 4 | 93.8 |
| 42 | 10 | AlCl₃-5.60 | toluene-50 | 95 | 5 | 88.1 |
| 43 | 10 | AlCl₃-5.60 | toluene-50 + H₂O (.03 g.) | 95 | 5 | 81.8 |
| 44 | 8.9 | AlCl₃-4.96 | toluene-45 | 90 | 5 | 100 |
| 45 | 9.3 | AlCl₃-5.20 + CH₃NO₂****-2.38 | toluene-50 | 90 | 6 | 85.1 |
| 46 | 12.87 | AlCl₃-7.20 | toluene-65 | 90–95 | 4 | 90.9 |
| 47 | 28.6 | AlCl₃-19.34 | toluene-117 | 95 | 4 | 84.6 |

*DEAC = diethyl aluminum chloride
**triethyl aluminim
***isolated yield
****p-nitromethane

EXAMPLE 48

Preparation of 4-(α-p-Toluyl-α-Cyano-Methyl)2,6-Di-t-Butyl Phenol

A mixture of 5.3 grams (0.025 mole) of 2,6-di-t-butylphenol, 25 milliliters of dimethylformamide, and sodium cyanide (4.9 grams; 0.1 mole) was charged to a round bottom reaction flask immersed in an oil bath and was heated to 140° C. (oil bath temperature) under nitrogen. A mixture of p-tolualdehyde (4.5 grams; 0.03 mole) in 15 milliliters of dimethylformamide was then added slowly to the flask over a period of time of approximately 3 hours. A dark green, bluish solution was observed. The reaction mixture was heated to 140° C. for 7 hours and then cooled to room temperature under nitrogen and left at room temperature overnight. The resultant reaction mixture was poured into an excess of water and extracted with diethyl ether. The ether layer was dried (MgSo4), filtered and the ether removed in a rotary evaporator to give 6.8 grams (81% yield) of 4-(α-p-toluyl-α-cyano-methyl)2,6-di-t-butyl phenol as identified by NMR using acrtylene tetrachloride as an internal standard.

EXAMPLE 49

Preparation of 4-(α-Benzyl-α-Cyano-Methyl)2,6-Di-t-butyl Phenol

A mixture of 2.06 grams (10 mmoles) of 2,6-di-t-butyl phenol, 10 milliliters of dimethylformamide and powdered sodium cyanide (1.96 grams; 40 mmoles) was charged to a round bottom flask immersed in an oil bath and heated to 140° C. (oil bath temperature) under nitrogen. A mixture of phenylacetaldehyde (1.8 grams; 15 mmoles) and 10 milliliters of dimethylformamide was then added slowly to the flask over a period of 2.5 hours. The resultant reaction mixture was cooled to ambient temperature and the mixture was poured into an excess of water and extracted with diethyl ether. The ether layer was dried (MgSO4), filtered and the ether removed in a rotary evaporator to give what was deemed to be 4-(α-benzyl-α-cyano-methyl)2,6-di-t-butyl phenol (35.5 area percent by VPC).

EXAMPLE 50

Preparation of 4-(α-Heptyl-α-Cyano-Methyl)2,6-Di-t-butyl Phenol

A mixture of 2,6-di-t-butyl phenol (2.06 grams; 10 mmoles), 10 milliliters of dimethylformamide and sodium cyanide (1.96 grams; 40 mmoles) was added to a round bottom flask immersed in an oil bath and was stirred at 140° C. (oil bath temperature) under nitrogen. Octylaldehyde (1.92 grams; 15 mmoles), in 5 milliliters of dimethylformamide was then added slowly to the flask over a period of time of 5 hours. The resultant reaction mixture was heated at 140° C. for 10 hours and then cooled to ambient temperature and poured into an excess amount of water. The reaction mixture was extracted with diethyl ether and the ether layer was dried (Na2SO4), filtered and the ether removed in a rotary evaporator to give 2.74 grams (82% yield) of 4-(α-heptyl-α-cyano-methyl)2,6-di-t-butyl phenol as identified by NMR using acetylene tetrachloride as an internal standard.

EXAMPLE 51

Preparation of 4-(α-p-Phenyl Phenyl-α-CyanoMethyl)2,6-Di-t-Butyl Phenol

A mixture of 2,6-di-t-butyl phenol (2.06 grams; 10 mmoles), 10 milliliters of dimethylformamide and powdered sodium cyanide (1.0 gram; 20 mmoles) was charged to a round bottom flask immersed in an oil bath and was stirred at 140° C. (oil bath temperature) under nitrogen. Next, approximately 1.2 grams (7 mmoles) of 4-phenylbenzaldehyde in 15 milliliters of dimethylformamide was added slowly to the flask over a period of time of 2 hours. The reaction mixture was maintained at 140° C. for 4.5 hours. Subsequent to this, an additional 7 mmoles of 4-phenylbenzaldehyde in 15 milliliters of dimethylformamide was added to the reaction mixture and the mixture was heated at 140° C. for 4 hours. The resultant reaction mixture was allowed to cool to ambient temperature and was poured into an excess amount of water and extracted with diethyl ether and the ether layer was dried (Na$_2$SO$_4$), filtered and the ether removed in a rotary evaporator to give 0.84 grams (42% yield) of 4-(α-p-phenyl phenyl-α-cyano-methyl)2,6-di-t-butyl phenol as identified by NMR using acetylene tetrachloride as an internal standard.

EXAMPLE 52

Preparation of 4-(α-Isopropyl-α-Cyano-Methyl)2,6-Dimethyl Phenol

A mixture of 2,6-dimethyl-phenol (1.22 grams; 10 mmoles), isobutyraldehyde (1.08 grams; 15 mmoles) sodium cyanide (0.74 grams; 15 mmoles) and 15 milliliters of methanol was charged to a Fischer-Porter tube immersed in an oil bath and pressurized to approximately 20 psig with nitrogen and heated to 140° C. (oil bath temperature) for 4 hours with stirring. The resultant reaction mixture was allowed to cool to ambient temperature and the mixture was stripped of methanol, and added to a 50 milliliter mixture of chloroform and water. The phases were separated and the organic layer was dried over Na$_2$SO$_4$, filtered and the chloroform removed to give 1.26 grams (62.4% yield) of 4-(α-isopropyl-α-cyano-methyl)2,6-dimethyl phenol as identified by NMR using acetylene tetrachloride as an internal standard.

EXAMPLE 53

Preparation of 4-(α-Isopropyl-α-Cyano-Methyl)2-t-Butyl Phenol

A mixture of 2-t-butyl phenol (1.5 grams; 10 mmoles), sodium cyanide (1.0 grams; 20 mmoles), 15 milliliters of methanol and isobutyraldehyde (1.08 grams; 15 mmoles) was charged to a 100 milliliter Fischer-Porter tube immersed in an oil bath and was pressurized to 20 psig with nitrogen and heated to 140° C. (oil bath temperature) for 8 hours. The resultant reaction mixture was allowed to cool to ambient temperature and an additional amount of isobutyraldehyde (3.6 grams; 50 mmoles) was added to the reaction mixture. The resultant mixture was heated to 140° C. under 20 psig of nitrogen for an additional 10 hours. Methanol was stripped from the mixture to give a residue containing a 75% yield of 4-(α-isopropyl-α-cyano-methyl)2-t-butyl phenol as identified by NMR using acetylene tetrachloride as an internal standard.

EXAMPLE 54

Preparation of α-Isopropyl-4-Hydroxphenylacetic Acid 4-(α-isopropyl-α-cyano-methyl)phenol (12.88 g.; 74 mmoles) was charged to a 30 ml. stainless steel autoclave along with 17.76 g. NaOH and 120 ml. water. The solution was heated at 130° C. for 6 hours with vigorous stirring while maintaining a pressure of between about 35 and 40 psig. After 6 hours, the reaction vessel was cooled to ambient temperature, the reaction mixture was discharged into a separatory funnel, and the pressure vessel was washed with 30 ml. of water which was added to the reaction mixture. The resultant mixture was washed with methylene chloride to remove residual tert-butyl toluene, cooled to ~10° C. and acidified to a pH between 2 and 3 with concentrated hydrochloric acid. The product was separated by filtration, washed with water and dried under pressure (20 mm. Hg/60° C.) to give 14.29 g. (96.0% yield) of α-isopropyl-4-hydroxyphenyl acetic acid as characterized by gas chromotograph.

In a manner similar to Example 54 above, a number of experiments were carried out varying the temperature, reaction time, pressure and ratio of reactants. The results were analyzed by HPLC using external standards and are shown in Table III.

TABLE III

| | Preparation of α-Isopropyl-4-Hydroxyphenylacetic Acid. | | | | | | |
|---|---|---|---|---|---|---|---|
| Experiment No. | 4-(α-isopropyl-α-cyano-methyl)-phenol (g.) | Catalyst (g.) | Solvent (ml.) | Temp. (°C.) | Pressure (psig) | Time (hr.) | % Yield |
| 55 | 1.152 | NaOH-1.39 | H$_2$O- 10 | reflux | ambient | 17 | 82.3 |
| 56 | 1.29 | NaOH-1.48 | H$_2$O- 10 | reflux | ambient | 17 | 100 |
| 57 | 9.77 | NaOH-13.48 | H$_2$O-100 | 130° | 35 | 6 | 85 |
| 58 | 10.89 | NaOH-15.6 | H$_2$O-100 | 130° | 35 | 6 | 86.6 |
| 59 | 14.27 | NaOH-19.7 | H$_2$O-110 | 130° | 35 | 5 | 87.5 |

Having disclosed the process of the present invention, one skilled in the art can readily envision various modifications and changes which are nevertheless within the scope of the invention. Therefore, it is desired that the process of this invention be limited only by the lawful scope of the appended claims.

We claim:

1. A process for the preparation of 4-(α-hydrocarbyl-α-cyano-methyl)2,6- di-substituted phenol having the formula

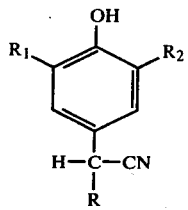

wherein R is selected from hydrogen, hydrocarbyl radicals, substituted hydrocarbyl radicals and hydrocarbyloxy radicals and $R_1$ and $R_2$ are the same or different monovalent substituents selected from the group consisting of alkyl, aralkyl and cyclic alkyl radicals which comprises reacting a di-substituted phenol having the formula

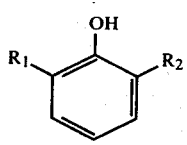

wherein $R_1$ and $R_2$ are as defined above with an aldehyde having at least one aldehyde radical and containing an R group as defined above and an alkali metal or an alkaline earth metal cyanide in a suitable reaction solvent to form said 4-(α-hydrocarbyl-α-cyano-methyl)2,6-di-substituted phenol.

2. The process o claim 1 wherein $R_1$ and $R_2$ are the same or different monovalent substituents selected from the group consisting of alkyl, aralkyl and cyclic alkyl radicals containing from 1 to about 40 carbon atoms.

3. The process of claim 1 wherein R is hydrogen or a hydrocarbyl radical containing up to 30 carbon atoms.

4. The process of claim 3 wherein R is a hydrocarbyl radical selected from alkyl, cycloalkyl, alkenyl, aralkyl, alkaryl and aryl.

5. The process of claim 3 wherein R is selected from hydrogen, methyl, ethyl, n-propyl and isopropyl.

6. The proess of claim 1 wherein the alkali metal cyanide is sodium cyanide.

7. The process of claim 1 wherein the solvent is a dipolar aprotic solvent.

8. The process of claim 7 wherein the solvent is selected from the group consisting of dimethyl sulfoxide, N,N-dimethylformamide, N,N-dimethylacetamide, dimethyl sulfone, tetramethylene sulfone, N-methylpyrrolidinone and acetonitrile.

9. The process of claim 7 wherein the solvent is selected from the group consisting of a lower alkanol having from 1 to about 6 carbon atoms.

10. The process of claim 1 wherein the reaction is carried out at an elevated temperature.

11. The process of claim 10 wherein the process is carried out at a temperature of at least 50° C.

12. A process for preparing α-hydrocarbyl-4-hydroxy-phenylacetic acid having the formula

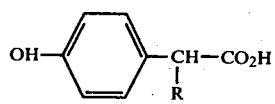

wherein R is selected from hydrogen, hydrocarbyl radicals, substituted hydrocarbyl radicals and hydrocarbyloxy radicals which comprises (i) preparing a 4-(α-hydrocarbyl-α-cyano-methyl)2,6-di-substituted phenol having the formula

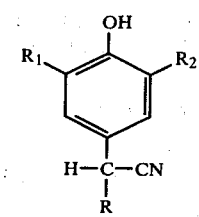

wherein R is as defined above and $R_1$ and $R_2$ are the same or different monovalent substituents selected from the group consisting of alkyl, aralkyl and cyclic alkyl radicals by reacting a di-substituted phenol having the formula

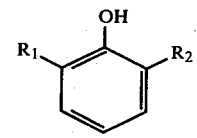

wherein $R_1$ and $R_2$ are as defined above with an aldehyde having at least one aldehyde radical and an R group as defined above and an alkali metal or an alkaline earth metal cyanide in a suitable reaction solvent to form said 4-(α-hydrocarbyl-α-cyano-methyl)2,6-di-substituted phenol, (ii) dealkylating the substituent groups ortho to the hydroxyl group from said 4-(α-hydrocarbyl-α- cyano-methyl)2,6-di-substituted phenol to form the corresponding 4-(α-hydrocarbyl-α-cyano-methyl)-phenol, and (iii) converting said 4-(α-hydrocarbyl-α-cyano-methyl)- phenol by hydrolysis to the corresponding α-hydrocarbyl-4-hydroxyphenylacetic acid.

13. The process of claim 12 wherein $R_1$ and $R_2$ are the same or different monovalent substituent selected from the group consisting of alkyl, aralkyl and cyclic alkyl radicals containing from 1 to about 40 carbon atoms.

14. The process of claim 12 wherein R is hydrogen or a hydrocarbyl radical containing up to 30 carbon atoms.

15. The process of claim 14 wherein R is a hydrocarbyl radical selected from alkyl, cycloalkyl, alkenyl, aralkyl, alkaryl and aryl.

16. The process of claim 14 wherein R is selected from hydrogen, methyl, ethyl, n-propyl and isopropyl.

17. The process of claim 12 wherein dealkylation is effected by heating said 4-(α-hydrocarbyl-α-cyano-methyl)2,6-di-substituted phenol at an elevated temperature in the presence of a dealkylation catalyst and an aromatic hydrocarbon.

18. The process of claim 17 wherein said dealkylation is carried out at a temperature of from about 60° C. to about 250° C.

19. The process of claim 17 wherein said dealkylation catalyst is selected from a phenoxy derivative of aluminum, megnesium, iron, zinc, phosphorus, zirconium, titanium, bismuth or tin.

20. The process of claim 17 wherein said aromatic hydrocarbon is selected from the group consisting of benzene, toluene, ethylbenzene, xylene, trimethyl benzene, tetrahydronaphthalene, isobutylbenzene, phenol, cresol, o-isopropylphenol, 4-hydroxyanisole, halobenzenes and aromatic ethers.

21. The process of claim 12 wherein dealkylation is carried out under an inert, nonreactive atmosphere.

22. The process of claim 12 wherein said hydrolysis is carried out in a basic medium.

23. The process of claim 22 wherein said hydrolysis is carried out in the presence of aqueous sodium hydroxide.

* * * * *